US007060659B2

(12) United States Patent
Killick et al.

(10) Patent No.: US 7,060,659 B2
(45) Date of Patent: *Jun. 13, 2006

(54) HERBICIDE COMPOSITION

(75) Inventors: Robert William Killick, Mount Waverley (AU); Andrew Robert Killick, Richmond (AU); Peter William Jones, Menzies Creek (AU); Peter Ronald Wrigley, Blackburn (AU); John David Morrison, Thomastown (AU)

(73) Assignee: Victorian Chemicals International Pty Ltd, Richmond (AU)

( * ) Notice: Subject to any disclaimer, the term of this patent is extended or adjusted under 35 U.S.C. 154(b) by 0 days.

This patent is subject to a terminal disclaimer.

(21) Appl. No.: 10/257,117

(22) PCT Filed: Oct. 17, 2001

(86) PCT No.: PCT/AU01/01310

§ 371 (c)(1),
(2), (4) Date: Oct. 8, 2002

(87) PCT Pub. No.: WO02/32227

PCT Pub. Date: Apr. 25, 2002

(65) Prior Publication Data

US 2003/0191026 A1   Oct. 9, 2003

(30) Foreign Application Priority Data

Oct. 17, 2000 (AU) .................................... PR0831
Apr. 10, 2001 (AU) .................................... PR4365

(51) Int. Cl.
*A01N 25/30* (2006.01)
*A01N 57/02* (2006.01)

(52) U.S. Cl. ...................... 504/206; 504/300; 504/306; 504/307; 504/320; 504/365

(58) Field of Classification Search ............... 504/206, 504/504, 127, 363, 128, 142, 144, 145, 323, 504/362, 300, 306, 307, 320, 365
See application file for complete search history.

(56) References Cited

U.S. PATENT DOCUMENTS

| | | | | |
|---|---|---|---|---|
| 3,799,758 A | * | 3/1974 | Franz | 504/206 |
| 4,154,596 A | | 5/1979 | George et al. | |
| 4,405,531 A | * | 9/1983 | Franz | 562/17 |
| 4,853,026 A | | 8/1989 | Frisch et al. | 71/86 |
| 4,984,874 A | | 1/1991 | Yamamoto et al. | 350/334 |
| 5,317,003 A | * | 5/1994 | Kassebaum et al. | 504/206 |
| 5,411,932 A | | 5/1995 | Yoshida et al. | 504/132 |
| 5,672,564 A | | 9/1997 | Wigger et al. | 504/116 |
| 6,117,816 A | * | 9/2000 | Jimoh et al. | 504/118 |
| 6,133,199 A | | 10/2000 | Soula et al. | 504/206 |
| 6,544,930 B1 | * | 4/2003 | Wright | 504/206 |
| 6,589,913 B1 | * | 7/2003 | Killick et al. | 504/206 |
| 2001/0019996 A1 | | 9/2001 | Soula et al. | 504/189 |

FOREIGN PATENT DOCUMENTS

| | | |
|---|---|---|
| AU | 77400/94 A | 5/1995 |
| AU | 674464 | 12/1996 |
| AU | 200021541 A | 6/2000 |
| AU | 200042761 | 11/2000 |
| EP | 0496145 * | 8/1992 |
| EP | 508 022 | 10/1992 |
| EP | 554 015 | 8/1993 |
| EP | 358 494 | 3/1994 |
| EP | 598 404 | 5/1994 |
| EP | 598 515 | 5/1994 |
| EP | 933 025 | 8/1999 |
| WO | WO 90/07272 | 7/1990 |
| WO | WO 93/00809 | 1/1993 |
| WO | WO 94/19941 A | 9/1994 |
| WO | WO 96/01049 | 1/1996 |
| WO | WO 97/00010 | 1/1997 |
| WO | WO 98/09518 | 3/1998 |
| WO | WO 98/17110 | 4/1998 |
| WO | WO 98/53680 | 12/1998 |
| WO | WO 99/00012 | 1/1999 |
| WO | WO 99/05914 | 2/1999 |
| WO | WO 99/51099 | 10/1999 |
| WO | WO 00/05953 | 2/2000 |
| WO | WO 00/32045 | 6/2000 |
| WO | WO 00/67571 | 11/2000 |

OTHER PUBLICATIONS

Roger S. Young, "Improve 'Promalin' Response with Adjuvants", *Proc Plant Growth Regul Work Group*, (1978), vol. 5, pp. 221-224.

Charles W. Coggins, et al., "Possible Methods to Increase Efficacy of Gibberellic Acid Applied to Navel Orange Trees", *Adjuvants for Agrichemicals*, Chapter 55, 1992, pp. 567-572.

(Continued)

*Primary Examiner*—S. Mark Clardy
(74) *Attorney, Agent, or Firm*—Drinker Biddle & Reath LLP; Daniel A. Monaco, Esq.

(57) ABSTRACT

There is provided an essentially non-aqueous homogeneous liquid herbicide composition comprising: a) a lipophilic solvent soluble complex comprising the reaction product of: i) not in excess of about 35% by weight of one or more lipophobic herbicides having an acidic moiety; and ii) not in excess of about 99% by weight of one or more tertiary dimethylamines of the structure $(CH_3)_2N$—R wherein R contains an alkyl group of at least 8 carbon atoms and may contain other chemical moieties and wherein is at least one mole equivalent of such amine to each mole of lipophobic herbicide; b) not in excess of about 60% by weight of one or more essentially non-aqueous polar solvents having low volatility; c) not in excess of about 90% by weight of one or more additional solvents selected from the group consisting of low to medium HLB surfactants; and d) not in excess of about 99% by weight of one or more lipophilic carriers.

42 Claims, No Drawings

OTHER PUBLICATIONS

P. M. Tabbush, et al., "Chemicals for the Forester: What about Additives", *Forestry and British Timber*, Feb. 1986, pp. 12-13.

D.J. Turner, "Additives for Use with Herbicides, a Review", AFRC Weed Research Organisation, *J. P. Pros. Troples 1984*, 1(2): 77-86,.

D.J. Turner, et al., "Studies with Solubilised Herbicide Formulations", Proceedings 12$^{th}$ British Weed Control Conference, (1974), pp. 177-185.

D.J. Turner, et al., "Studies with Alternative Glyphosate Formulations", 1985 BCPC Monogram No. 28, Symposioum on Application and Biology, pp. 2-13.

D.J. Turner, "Preliminary Results of Research into Improving Herbicide Performance by the Use of Additives", Weed Reserach Organization, Oxford, UK, 1976, pp. 82-91.

Derwent-ACC-No. 1983-49777K (Feb 12, 1983), Abstracting JP 58023898 A, dated Feb. 12, 1983.

\* cited by examiner

HERBICIDE COMPOSITION

FIELD OF THE INVENTION

The invention relates to herbicide compositions. More particularly, the invention relates to essentially non-aqueous homogeneous herbicide compositions comprising lipophilic solvent soluble complexes for application without dilution in water.

BACKGROUND OF THE INVENTION

In this specification, where a document, act or item of knowledge is referred to or discussed, this reference or discussion is not to be taken as an admission that the document, act or item of knowledge or any combination thereof was at the priority date:

(a) part of common general knowledge; or
(b) known to be relevant to an attempt to solve any problem with which this specification is concerned.

A herbicide composition typically has to be in a form from which it is available to act upon the target. If, for example, a herbicide composition is sprayed on a plant and the carrier evaporates, the herbicide can be left solid and essentially unavailable for uptake.

Whilst the following discussion concerns glyphosate, it is to be understood that the same principles apply to all lipophobic herbicides having an acidic moiety.

Glyphosate is a non-selective herbicide which is applied in aqueous solutions to control weeds in agricultural, industrial and domestic situations. There has also been development of crops which are resistant to herbicides, such as glyphosate and glufosinate, so that the herbicides may be used post emergent to protect the crop. In this specification, the term "glyphosate" refers to N-(phosphonomethyl)glycine CAS No. [1071-83-6]. Currently, glyphosate is neutralised by a base, such as isopropylamine, to allow it to be carried in an aqueous system.

Adjuvants are commonly used with these aqueous glyphosate compositions to improve the efficacy or induce other desirable properties. Adjuvants can be either formulated into commercial ready-to-use glyphosate-containing products or sold as additives to be added to the tank mix. These adjuvant materials include (i) surfactants and/or oils for wetting, spreading and spray retention, (ii) buffering agents and water conditioners for protecting the glyphosate and (iii) polymeric materials which may reduce spray drift.

Sometimes the adjuvant is lipophilic, such as petroleum oils, vegetable oils or esterified oils, and, in these circumstances, an emulsifying system is also typically necessary to enable the hydrophobic adjuvant to form an emulsion with the aqueous glyphosate composition. When used with lipophilic adjuvants and/or oil carriers, the glyphosate is expected to remain in the aqueous phase and may not fully benefit from the use of such a lipophilic adjuvant.

There have been attempts to improve the efficiency of glyphosate which include the use of higher molecular weight amines to form a salt with the glyphosate. However, most of these attempts with salts of higher molecular weight amines were focused on the conventional glyphosate application system wherein the product is diluted in water for use. The amines which are described in these attempts include primary, secondary and tertiary amines.

The authors are aware of only one attempt to form essentially non-aqueous compositions of herbicides and these compositions were intended for application by electrostatic spraying. This attempt teaches the preferred use of a stoichiometric amount of a primary alkyl amine having 13 to 17 carbon atoms to form a salt with the herbicide. It also teaches the use of a significant portion of a volatile polar solvent in the formation of the salt and the composition which is applied.

Current spray application technology enables the application of essentially non-aqueous agrochemical compositions as well as aqueous compositions. Oil-soluble (lipophilic) insecticides and herbicides can be diluted in lipophilic carriers, such as petroleum or vegetable-based oils for spraying rather than dilution in water. By choosing appropriate lipophilic carriers, some of the inefficiencies associated with aqueous spray mixtures, such as droplets reflecting off the target, in-flight evaporation and droplet dry-down, can be minimised. Rainfastness of the active may also be a problem for some products where the active constituent may be washed off the target by rain some hours after application but before it has been adequately taken up. Other benefits which may be achieved using non-aqueous carriers include enhanced uptake into the target and reduced spray volumes.

Herbicide compositions are also applied using planes or helicopters. Much of the cost of aerial spraying is associated with the aircraft set up and flying time, hence to be able to spray highly concentrated compositions over a larger area without reloading multiple times allows for more efficient use of aircraft.

Glyphosate and other lipophobic herbicides, such as glufosinate, are basically insoluble in lipophilic carriers which would allow exploitation of the lower spray volumes. Thus, there has been a need to develop an essentially non-aqueous carrier system with low volatility for a lipophobic herbicide such as glyphosate.

SUMMARY OF THE INVENTION

It has been found that it is possible to prepare an essentially non-aqueous herbicide composition where a lipophobic herbicide, such as glyphosate, is dissolved in a lipophilic carrier using hydrophobic tertiary amines to form a lipophilic solvent soluble complex. The lipophobic herbicide is not dissolved in an aqueous carrier or in an aqueous carrier dispersed in a lipophilic carrier. The essentially non-aqueous herbicide composition is then suitable for use without dilution in water and may provide a variety of benefits including reduced spray volumes, improved efficacy and rainfastness.

In order to minimise inefficiencies such as in-flight evaporation, the choice of the non-aqueous carrier involves the balance of many factors such as viscosity and volatility. It has further been found that the use of tertiary amines with the lipophobic herbicide enables the use of non-volatile polar solvents. This minimises the possibility that evaporation of the polar solvent will leave the lipophobic herbicide solid on the leaf and essentially unavailable for uptake.

The herbicide composition according to the invention is suitable for spraying from all known spraying technology including conventional technology used with aqueous solutions.

According to a first aspect of the invention, there is provided an essentially non-aqueous homogeneous liquid herbicide composition comprising:

(a) a lipophilic solvent soluble complex comprising the reaction product of:
  (i) not in excess of about 35% by weight of one or more lipophobic herbicides having an acidic moiety; and (ii) not in excess of about 99% by weight of one or more tertiary dimethylamines of the structure $(CH_3)_2$N—R wherein R contains an alkyl group of at least 8 carbon atoms and may contain other chemical moieties and wherein there is at least one mole equivalent of such amine to each mole of lipophobic herbicide;

(b) not in excess of about 60% by weight of one or more essentially non-aqueous polar solvents having low volatility;

(c) not in excess of about 90% by weight of one or more additional solvents selected from the group consisting of low to medium HLB surfactants; and (d) not in excess of about 99% by weight of one or more lipophilic carriers.

All proportions are by weight unless otherwise indicated.

The reaction product (a) may be an isolatable product of the reaction of (i) and (ii) or may be formed in situ.

The lipophobic herbicide having an acidic moiety has a chemical structure which includes one or more acid moieties and is therefore capable of reacting with a proton acceptor. Where used herein the term "acid" refers to the Brönsted-Lowry definition of an acid. The term "lipophobic herbicide" therefore includes zwitterionic substances. Examples include glyphosate, glufosinate, bilanafos, fosamine or any other lipophobic herbicide which forms a lipophilic solvent soluble complex with the tertiary amines.

The amount of lipophobic herbicide reacted to form the lipophilic solvent soluble complex is calculated by reference to the free form of the lipophobic herbicide as the active ingredient. The amount of lipophobic herbicide in the composition will typically be determined by the spray rate (liters of spray solution per hectare) and the amount of lipophobic herbicide required to achieve suitable effects. For example, glyphosate is usually sprayed at 250 to 1000 g/ha with a spray rate of 50 to 100 L/ha or at ultra low volume rates of 2 to 25 l/ha. Preferably, the amount of lipophobic herbicide is not in excess of 25%. More preferably, the amount of lipophobic herbicide is in the range of from 0.1 to 10.0% by weight When glyphosate is used, the combination of (i) and (ii) may be considered by some to be mono-, di- or tri- amine salts of glyphosate and such combinations, however prepared, may be used as the source of glyphosate in this composition.

Tertiary amines which are sterically hindered such as tributylamine or didecylmethylamine do not form suitably stable complexes with the lipophobic herbicides. It has also been found that the complexes formed between lipophobic herbicides and amines with considerably less steric hindrance such as primary and secondary alkylamines are difficult to solubilise in lipophilic carriers, prone to crystallisation in essentially non-aqueous environments and require significant amounts of polar solvent to remain liquid in a lipophilic carrier. It is thus surprising that the preferred amines for forming lipophilic solvent soluble complexes with lipophobic herbicides such as glyphosate are tertiary dimethylamines.

The tertiary dimethylamines are of the structure $(CH_3)_2$N—R wherein R contains an alkyl group of at least 8 carbon atoms and may contain other chemical moieties. For example, the tertiary dimethylamines may be selected from dimethylalkylamines or other substituted alkyldimethylamines such as alkylamidoalkyldimethylamines. Examples of such tertiary dimethylamines are dimethylcocoamine and oleylamidopropyldimethylamine.

Provided that there is at least one mole equivalent of tertiary dimethylamines per mole of lipophobic herbicide, it is possible to use lower amines to react with any remaining acidic moieties on the lipophobic herbicide. Excess amine may be used. Preferably, more than one mole equivalent of tertiary dimethylamine is used per mole of glyphosate because the lipophilic nature of the complex with the lipophobic herbicide increases such that it becomes even easier to dissolve in a chosen lipophilic carrier. The relative amount of additional solvent required to aid in solubilising the complex is also reduced. Therefore, highly concentrated compositions suited to ultra low volume spraying are possible as there is less additional solvent in proportion to the complex in order to dissolve it in a small amount of lipophilic carrier. Preferably, the amount of amine is in the range of from 1 to 50% by weight. More preferably, the amount of amine is in the range of from 10 to 25% by weight.

The essentially non-aqueous polar solvents having low volatility may be selected from solvents available to those skilled in the art, for example, butane-1,3-diol, hexylene glycol, 2-ethylhexanol or dipropyleneglycol monomethyl ether. These polar solvents are necessary for the formation of the lipophilic complex of the lipophobic herbicide with the tertiary dimethylamine and subsequent stability of the herbicide composition as a liquid. Typically, the amount of polar solvent is in the range from equal weight to lipophobic herbicide to twice the lipophobic herbicide weight. In a ready-to-use formulation preferably the amount of essentially non-aqueous polar solvents which have low volatility is in the range of from 1 to 10% by weight.

Small portions of volatile polar solvents such as water, ethanol or isopropanol may be used to assist the action of the essentially non-aqueous polar solvents having low volatility. Such volatiles may later be readily removed from the composition if desired. Since these volatile solvents are used in small proportions the overall stability of the composition is not detrimentally effected if the volatile solvent evaporates in use.

The types of reagents which may be used as additional solvents are defined by reference to the term "surfactant", however, it is not necessary that these substances exhibit typical surfactant characteristics when used in the composition particularly given that they are used without dilution in water. All surfactants consist of a molecule that combines both hydrophilic and lipophilic groups. The HLB of a surfactant is an expression of its Hydrophile-Lipophile-Balance, that is, the balance of the size and strength of the hydrophilic and lipophilic groups of the emulsifiers. A surfactant that is predominantly lipophilic is assigned an HLB number in the range 0–10 and a surfactant which is predominantly hydrophilic is assigned a higher HLB number above 10.

Examples of suitable surfactants with a low to medium HLB which may be used as additional solvents are mono and di-glycerides of fat forming fatty acids (glycerol monooleate or glycerol dioleate), partial fatty acid esters of sorbitol anhydrides (sorbitan monooleate or sorbitan monolaurate), partial fatty acid esters of other polyols such as pentaerythritol, polyglycerol and sugar pentitols, hexitols and their anhydrides and lecithin. Further examples include low mole nonionic ethoxylates with alkyl or arylalkyl of 12 to 21 carbon atoms and 2 to 9 moles ethylene oxide adducted, such as Teric 12A3 (C12 or C12–15 alcohol with 3 moles ethylene oxide) and Teric DD5 (dodecylphenol with 5 moles ethyleneoxide). Still further examples include fatty alkanolamides such as oleic diethanolamide, organopolysiloxanes or alkylpolyglycosides Preferably, there is not in excess of 50% by weight of additional solvents. More preferably, the amount of additional solvents is in the range of from 0.4 to 40.0% by weight. The very low levels of these additional solvents will be present if commercial spray oil is used as the lipophilic carrier since adjuvant compositions such as crop oil concentrates or other self-emulsifying oil-based compositions already contain these surfactants. The amount of additional solvent used from half of the-combined weight of lipophobic herbicide, amine and polar solvent to about 1.5 times this weight.

The lipophilic carrier may be any suitable lipophilic carriers known to those skilled in the art. For example, the lipophilic carrier may be petroleum fractions, vegetable oils, synthetic triglycerides, alkyl esters of fatty acids, fatty alcohols, guerbet alcohols or any mixture thereof. Preferably, the lipophilic carriers are aliphatic paraffinic light distillates or vegetable oils and their derivatives. Typically, a petroleum fraction is used as it has been cost effective. These fractions, for example, can be 70, 100 or 150 second solvent neutral. Preferably, there is not in excess of 99% by weight of lipophilic carrier. If the composition is applied to herbicide resistant crops, then preferably, the lipophilic carrier is low in aromatics. Vegetable oils and their derivatives may be preferred for ecological reasons. The choice of the lipophilic carrier may be influenced by its viscosity and the spray application technology.

In another embodiment of the invention, the herbicide composition is a concentrated composition comprising reagents (a) and (b), which could itself be sprayed or it could be diluted later with an essentially non-aqueous carrier such as reagent (c) and optionally (d). For example, the concentrated composition could be sold in containers of convenient size and farmers could then dilute the composition with a crop oil concentrate as desired for the spraying technique to be used. The invention includes a concentrate composition comprising additional solvents wherein the additional solvents may act as the carrier. Such compositions may be sprayed without addition of further solvent or may be diluted with an essentially non-aqueous lipophilic carrier. Where little or no lipophilic carrier is added then lesser amounts of additional solvents are appropriate and facilitate the more concentrated lipophobic herbicide preparations used in ultra low volume spraying.

The following table sets out the proportions of components which are typical for essentially non-aqueous glyphosate compositions intended for conventional volume, low volume and ultra low volume spray application.

Similar principles apply to the formation of lipophilic compositions based on complexes of glufosinate.

fungicides and insecticides. For example, 2,4-D may be added to the composition. In some situations, glyphosate, for example, alone is not sufficient to address the farmer's needs and a lipophilic herbicide is combined with the glyphosate composition.

In another preferred form of the invention, the herbicide composition further comprises one or more other available adjuvant components. The adjuvant component may be selected from plant nutrients, spray drift retardants, stickers, spreaders or viscosity modifiers.

Non-aqueous solutions of lipophobic herbicides can thus be formed for spray application in situations where water evaporation or spray volume may be an issue.

According to a second aspect of the invention, there is provided a method for improving rainfastness of a lipophobic herbicide comprising the step of formulating the lipophobic herbicide in an essentially non-aqueous composition comprising:
(a) a lipophilic solvent soluble complex comprising the reaction product of:
(i) not in excess of about 35% by weight of one or more lipophobic herbicides having an acidic moiety; and
(ii) not in excess of about 99% by weight of one or more tertiary dimethylamines of the structure $(CH_3)_2N$—R wherein R contains an alkyl group of at least 8 carbon atoms and may contain other chemical moieties and wherein there is at least one mole equivalent of such amine to each mole of lipophobic herbicide;
(b) not in excess of about 60% by weight of one or more essentially non-aqueous polar solvents having low volatility;
(c) not in excess of about 90% by weight of one or more additional solvents selected from the group consisting of low to medium HLB surfactants; and
(d) not in excess of about 99% by weight of one or more lipophilic carriers.

According to a third aspect of the invention, there is provided a method for treating weeds comprising the step of applying an essentially non-aqueous herbicide composition comprising:
(a) a lipophilic solvent soluble complex comprising the reaction product of:
(i) not in excess of about 35% by weight of one or more lipophobic herbicides having an acidic moiety; and
(ii) not in excess of about 99% by weight of one or more tertiary dimethylamines of the structure $(CH_3)_2N$—R wherein R contains an alkyl group of at least

| Component | conventional volume spray application 50–100 l/ha | | | low volume spray application 25–50 l/ha | | | ultra low volume spray application 2–25 l/ha | | |
|---|---|---|---|---|---|---|---|---|---|
| | min | typical | max | min | typical | max | min | typical | max |
| glyphosate | 0.1 | 1 | 5 | 0.1 | 2 | 10 | 0.2 | 5 | 25 |
| 3° amine | 0.1 | 4 | 25 | 0.4 | 8 | 40 | 0.8 | 15 | 50 |
| polar solvent | 0.1 | 1 | 10 | 0.1 | 2 | 20 | 0.2 | 5 | 50 |
| additional solvent | 0.1 | 9 | 30 | 1 | 15 | 90 | 2 | 25 | 90 |
| lipophilic carrier | 50 | 85 | 99 | 0 | 73 | 98 | 0 | 50 | 95 |

In another preferred form of the invention, the herbicide composition further comprises one or more pesticides which are compatible with the lipophilic nature of the herbicide composition. The term "pesticides" includes herbicides, 8 carbon atoms and may contain other chemical moieties and wherein there is at least one mole equivalent of such amine to each mole of lipophobic herbicide;

(b) not in excess of about 60% by weight of one or more essentially non-aqueous polar solvents having low volatility;

(c) not in excess of about 90% by weight of one or more additional solvents selected from the group consisting of low to medium HLB surfactants; and (d) not in excess of about 99% by weight of one or more lipophilic carriers.

According to a fourth aspect of the invention, there is provided a method for preparing an essentially non-aqueous sprayable herbicide composition comprising the steps of (a) combining the following reagents:
(i) not in excess of about 35% by weight of one or more lipophobic herbicides having an acidic moiety; and
(ii) not in excess of about 99% by weight of one or more tertiary dimethylamines of the structure $(CH_3)_2$N—R wherein R contains an alkyl group of at least 8 carbon atoms and may contain other chemical moieties and wherein there is at least one mole equivalent of such amine to each mole of lipophobic herbicide; and
(iii) not in excess of about 60% by weight of one or more essentially non-aqueous polar solvents having low volatility;

(b) combining the mixture formed in (a) with not in excess of about 90% by weight one or more additional solvents selected from the group consisting of low to medium HLB surfactants and not in excess of about 99% by weight one or more lipophilic carriers.

Preferably, the reagents in step (a) are combined with heating/stirring. Reflux conditions may be used where appropriate. Preferably, the combining in step (b) comprises stirring the mixture whilst warm.

In a further embodiment, the lipophilic solvent soluble complex is prepared and isolated from the essentially non-aqueous polar solvent prior to its use. This is useful where the essentially non-aqueous polar solvent being used is inconvenient as a component of the herbicide composition, for example, due to product registration requirements, and it is preferable that it be removed.

According to a fifth aspect of the invention, there is provided an essentially non-aqueous homogeneous liquid herbicide composition comprising:

(a) a lipophilic solvent soluble complex comprising the reaction product of:
(i) not in excess of about 35% by weight of one or more lipophobic herbicides having an acidic moiety; and
(ii) not in excess of about 99% by weight of one or more tertiary dimethylamines of the structure $(CH_3)_2$N—R wherein R contains an alkyl group of at least 8 carbon atoms and may contain other chemical moieties and wherein there is at least one mole equivalent of such amine to each mole of lipophobic herbicide; and (b) not in excess of about 60% by weight of one or more essentially non-aqueous polar solvents which assist the formation of the lipophilic solvent soluble complex, wherein the complex is formed in the presence of the essentially non-aqueous polar solvent but the essentially non-aqueous polar solvent may be removed after formation of the complex if desired.

According to a sixth aspect of the invention, there is provided an essentially non-aqueous homogeneous liquid herbicide composition comprising:

(a) a lipophilic solvent soluble complex comprising the reaction product of:
(i) not in excess of about 35% by weight of one or more lipophobic herbicides having an acidic moiety; and
(ii) not in excess of about 99% by weight of one or more tertiary dimethylamines of the structure $(CH_3)_2$N—R wherein R contains an alkyl group of at least 8 carbon atoms and may contain other chemical moieties and wherein there is at least one mole equivalent of such amine to each mole of lipophobic herbicide;

(b) not in excess of about 90% by weight of one or more additional solvents selected from the group consisting of low to medium HLB surfactants; and (c) not in excess of about 99% by weight of one or more lipophilic carriers.

It has also been found that it is possible to use a lower amount of tertiary dimethylamines and still obtain an essentially non-aqueous homogeneous liquid herbicide composition.

According to a seventh aspect of the invention there is provided an essentially non-aqueous homogeneous liquid herbicide composition comprising:

(a) a lipophilic solvent soluble complex comprising the reaction product of:
(i) not in excess of about 50% by weight of one or more lipophobic herbicides having an acidic moiety; and
(ii) not in excess of about 99% by weight of one or more tertiary dimethylamines of the structure $(CH_3)_2$N—R wherein R contains an alkyl group of at least 8 carbon atoms and may contain other chemical moieties, wherein there is less than one mole equivalent of such amines to each mole of lipophobic herbicide;
(iii) not in excess of about 20% by weight of one or more hydrophilic amines;
wherein the total mole equivalents of the amines in (ii) and (iii) is at least equivalent to the moles of lipophobic herbicide;

(b) not in excess of about 60% by weight of one or more essentially non-aqueous polar solvents having low volatility;

(c) not in excess of about 90% by weight of one or more additional solvents selected from the group consisting of low to medium HLB surfactants; and (d) not in excess of about 99% by weight of one or more lipophilic carriers.

Examples of hydrophilic amines include those conventionally used with aqueous glyphosate preparations, eg. Isopropylamine, diethanolamine and monoethanolamine.

EXAMPLES

The invention will now be further illustrated and explained in the following non-limiting examples.

The following components were used

| | |
|---|---|
| Ammonium nitrate (adjuvant component) | Ex Orica, Australia |
| Break-thru OE 444 (additional solvent) | Organosilicon ex Goldschmidt, USA |
| BS 1000 (used in control treatments) | Commercial wetting agent ex Cropcare, Australia |
| 1,3-butanediol (polar solvent) | Ex Hoechst Celanese, USA |
| 2,4-D (herbicide) | 2,4-D acid ex Unisun, China |
| Diethanolamine (hydrophilic amine) | Ex Union Carbide |

-continued

| | |
|---|---|
| Dimethylcocoamine (tertiary dimethylamine) | Ex Proctor & Gamble, USA |
| Esterol 123 (lipophilic solvent) | Ethyl oleate (80% ethyl/20% methyl) ex Victorian Chemical Company, Australia |
| Esterol 272 (additional solvent) | Glyceryl mono-oleate ex Victorian Chemical Company, Australia |
| Ethanol (volatile solvent) | Anhydrous, 100SGF3 grade methanol denatured ex CSR, Australia |
| Glufosinate (lipophobic herbicide) | 3-amino-3-(carboxypropyl)methyl-phosphonic acid ex Aventis, |
| Glyphosate (lipophobic herbicide) | N-(phosphonomethyl)glycine (98% minimum) ex Davison Industries, Australia or Unisun Chemicals, China |
| Glysolv DPM (polar solvent) | Dipropyleneglycol monomethyl ether ex Huntsman, Australia |
| Hexylene glycol (polar solvent) | Ex Tiger Chemicals, Australia |
| Iso-octanol (polar solvent) | Ex Bentley-Chemplax, Australia |
| Monoethanolamine (hydrophilic amine) | Ex Union Carbide |
| Oleylamidopropyldimethylamine (tertiary dimethylamine) | Prepared by reaction of oleic acid with N,N-dimethylaminopropylamine at Victorian Chemical Company, Australia |
| Phosphoric acid 81% aqueous | Ex Deltrex Chemicals, Australia |
| Prorex 36 (lipophilic carrier) | 100 solvent neutral mineral oil Ex Mobil, Australia |
| Shell P878 (lipophilic carrier) | 300 test kerosene ex Shell, Australia |
| Span 80 (additional solvent) | Sorbitan mono-oleate ex Huntsman Corporation, Australia |
| Teric 12A3 (additional solvent) | C12–15 synthetic alcohols and 3 moles ethylene oxide ex Huntsman Corporation, Australia |
| Teric DD5 (additional solvent) | dodecylphenol and 5 moles ethylene oxide ex Huntsman Corporation, Australia |
| Terwet 3001 (additional solvent) | Alkyl polyglucoside ex Huntsman, Australia |
| Vicamid 825 (additional solvent) | Oleyldiethanolamide ex Victorian Chemical Company, Australia |
| VOC RHT 70 (lipophilic carrier) | 70 solvent neutral mineral oil ex Safety-Kleen, USA |

Example 1

62.5 parts dimethylcocoamine, 15 parts glyphosate, 15 parts 1,3-butanediol and 7.5 parts ethanol were refluxed together for 15 minutes to form a single phase liquid with about 15% of glyphosate present.

This formulae is useful when high glyphosate content is required. For example, this formula is appropriate for use in ultra low volume crop spraying.

Example 2

The following compositions were prepared and resulted in clear liquids containing about 7.5% glyphosate. The dimetbylcocoamine, ethanol and glyphosate were refluxed together to form a single phase liquid. The additional solvent was then added and mixing continued at 40 to 70° C. These compositions may be used for ultra low volume spray application directly. They are also soluble in VOC RHT 70 and therefore can be converted to compositions suitable for low volume spray application. However, loss of ethanol from these formulations resulted in unstable compositions.

| Composition | 1 | 2 | 3 |
|---|---|---|---|
| Dimethylcocoamine | 33 | 33 | 33 |
| Ethanol | 9 | 9 | 9 |
| Glyphosate | 7.5 | 7.5 | 7.5 |
| Span 80 | — | — | 50.5 |
| Teric DD5 | — | 50.5 | — |
| Teric 12A3 | 50.5 | — | — |

Example 3

32 parts dimethylcocoamine, 8 parts 1,3-butanediol and 8 parts glyphosate were mixed together at 60° C. for one hour. 24 parts Span 80, 2 parts Glysolv DPM and 26 parts Esterol 272 were then added and mixing continued at 40 to 70° C. until a clear liquid was formed with about 8% glyphosate acid.

This composition is soluble in VOC RHT 70 if a more dilute composition is desired.

Use of 1,3-butanediol rather than ethanol minimised the vapour loss during formation of the composition.

Example 4

2 parts glyphosate was combined with 8 parts dimethylcocoamine and 4 parts ethanol and refluxed with stirring until clear to form Mixture A. When cooled, Mixture A was a liquid paste with about 14–15% glyphosate.

20 parts of Esterol 272 was added to Mixture A and warmed at 30 to 50° C. with stirring until clear to form Mixture B. When cooled, Mixture B was a clear viscous liquid with about 5–6% glyphosate.

34 parts of Mixture B was combined with 66 parts of VOC RHT 70 to provide a clear liquid with 2% glyphosate.

If 340 parts of Mixture B is diluted to 1 liter with VOC RHT 70, a preparation containing 2% w/v suitable for spraying is obtained.

If 340 parts of Mixture B is diluted to 4 liters with VOC RHT 70, a preparation containing 0.5% w/v suitable for spraying is obtained.

Example 5

79 parts of dimethylcocoamine was combined with 21 parts of glyphosate and 40 parts ethanol and refluxed until a clear solution was formed. 210 parts of Esterol 272, 15 parts of Break-thru OE 444 and 635 parts of VOC RHT 70 were added with mixing at 30 to 50° C. The final product was a clear liquid with about 2% glyphosate present.

Example 6

90 parts of dimethylcocoamine was combined with 20 parts glyphosate and 30 parts ethanol and refluxed until a clear solution was formed. 195,parts of Esterol 272, 15 parts Teric DDS (or Teric 12A3) and 650 parts VOC RHT 70 were then added with mixing at 30 to 50° C. The final product was 1000 parts of a clear liquid with about 2% glyphosate present.

This formulation enables farmers and/or aerial operators to use self-emulsifying mineral oil compositions that contain surfactants, such as crop oil concentrates, as the lipophilic carrier when preparing the composition.

Example 7

Glyphosate (50 parts), 1,3-butanediol (50 parts), ethanol (50 parts) and dimethylcocoamine (132 parts, approximately 2.14 molar equivalent to glyphosate) were refluxed at 80–90° C. with stirring for 90 minutes until clear to form Mixture C. Mixture C was a clear liquid with 17–18% glyphosate.

Mixture C (20 parts) was combined with Esterol 272 (30 parts) to provide a clear liquid with 7% glyphosate.

Mixture C (24 g) was combined with Esterol 272 (36 g) and a sufficient amount of Shell P878 to provide 200 ml of a clear liquid with 2% w/v glyphosate.

Example 8

Glyphosate (50 parts), 1,3-butanediol (50 parts), ethanol (50 parts), dimethylcocoamine (71 parts, approximately 1.07 molar equivalent to glyphosate) and water (20 parts) were refluxed at 80–90° C. with stirring for one hour. Esterol 272 (118 parts), Vicamid 825 (66 parts) and Span 80 (57 parts) were then added and the mixture warmed with stirring to form Mixture D, a clear liquid with 10–11% glyphosate.

Mixture D (40g) was combined with a sufficient amount of Shell P878 to form 200 ml of a clear liquid with 2% w/v glyphosate.

Example 9

In this example, compositions containing different lipophobic herbicides were tested. The amount of herbicide per hectare was lowered to below the typical application rate to enable an assessment of the difference effectiveness of the compositions.

The inclusion of non-volatile polar solvents was considered essential for these and subsequent formulations following instability problems noted with earlier compositions upon loss of ethanol.

The following compositions were tested.

| Composition | Lipophobic herbicides (g/L) | | Dimethylcocoamine (g/L) | Polar solvent (g/L) | | Additional solvent (g/L) | | Lipophilic carrier (to 1 litre) |
|---|---|---|---|---|---|---|---|---|
| 4. | Glyphosate (25 g/ha) | 2.59 | 3.69 | 1,3-butanediol | 2.59 | Esterol 272 | 31.1 | VOC RHT 70 |
| | | | | Ethanol | 2.59 | Span 80 | 2.95 | |
| | | | | Water | 1.04 | Vicamid 825 | 3.42 | |
| 5. | Glyphosate (75 g/ha) | 7.68 | 10.91 | 1,3-butanediol | 7.68 | Esterol 272 | 64.07 | VOC RHT 70 |
| | | | | Ethanol | 7.68 | Span 80 | 8.75 | |
| | | | | Water | 3.06 | Vicamid 825 | 10.14 | |
| 6. | Glyphosate (150 g/ha) | 15.36 | 21.82 | 1,3-butanediol | 15.36 | Esterol 272 | 68.14 | VOC RHT 70 |
| | | | | Ethanol | 15.36 | Span 80 | 17.5 | |
| | | | | Water | 6.12 | Vicamid 825 | 20.28 | |
| 7. | Glyphosate (25 g/ha) | 2.57 | 7.29 | 1,3 butanediol | 2.57 | Esterol 272 | 30 | VOC RHT 70 |
| | | | | Ethanol | 2.57 | | | |
| 8. | Glyphosate (75 g/ha) | 7.71 | 21.87 | 1,3 butanediol | 7.71 | Esterol 272 | 50 | VOC RHT 70 |
| | | | | Ethanol | 7.71 | | | |
| 9. | Glyphosate (150 g/ha) | 15.42 | 43.74 | 1,3 butanediol | 15.42 | Esterol 272 | 60 | VOC RHT 70 |
| | | | | Ethanol | 15.42 | | | |
| 10. | Glyphosate (25 g/ha) | 2.57 | 10.26 | 1,3 butanediol | 2.97 | Vicamid 825 | 60 | VOC RHT 70 |
| | | | | Water | 50 | Teric 12A3 | 65 | |
| 11. | Glyphosate (75 g/ha) | 7.71 | 30.87 | 1,3 butanediol | 8.92 | Vicamid 825 | 80 | VOC RHT 70 |
| | | | | Water | 50 | Teric | 65 | |
| 12. | Glyphosate (25 g/ha) | 2.57 | 10.26 | 1,3 butanediol | 2.97 | Esterol 272 | 24.2 | Esterol 123 |
| 13. | Glyphosate (75 g/ha) | 7.71 | 30.87 | 1,3 butanediol | 8.92 | Esterol 272 | 52.5 | Esterol 123 |
| 14. | Glyphosate (150 g/ha) | 15.42 | 61.73 | 1,3 butanediol | 17.85 | Esterol 272 | 65 | Esterol 123 |
| 15. | Glyphosate (25 g/ha) | 2.57 | 10.26 | 1,3 butanediol | 2.97 | Esterol 272 | 34.2 | VOC RHT 70 |
| 16. | Glyphosate (75 g/ha) | 7.71 | 30.87 | 1,3 butanediol | 8.92 | Esterol 272 | 52.5 | VOC RHT 70 |
| 17. | Glyphosate (150 g/ha) | 15.42 | 61.73 | 1,3 butanediol | 17.85 | Esterol 272 | 80 | VOC RHT 70 |
| 18. | Glufosinate (50 g/ha) | 5 | 30 | 1,3 butanediol | 15 | Esterol 272 | 124 | VOC RHT 70 |
| 19. | Glufosinate (200 g/ha) | 20 | 120 | 1,3 butanediol | 60 | Esterol 272 | 183 | VOC RHT 70 |

-continued

| Composition | Lipophobic herbicides (g/L) | | Dimethylcocoamine (g/L) | Polar solvent (g/L) | | Additional solvent (g/L) | | Lipophilic carrier (to 1 litre) |
|---|---|---|---|---|---|---|---|---|
| 20. | Glyphosate (75 g/ha) 2,4-D (75 g/ha) | 7.5 7.52 | 37.5 | 1,3 butanediol | 11.25 | Esterol 272 | 86.25 | VOC RHT 70 |
| 21. | Glyphosate (150 g/ha) 2,4-D (150 g/ha) | 15 15 | 75 | 1,3 butanediol | 22.50 | Esterol 272 | 122.5 | VOC RHT 70 |
| 22. | Glyphosate (75 g/ha) 2,4-D (150 g/ha) | 7.5 15 | 45 | 1,3 butanediol | 20 | Esterol 272 | 90 | VOC RHT 70 |

The following control treatments were used. Glyphosate refers to Glyphosate CT (containing 450 g/l glyphosate as the isopropylamine salt), 2,4-D refers to Amicide 500 (containing 2,4-D 500 g/l as the dimethylamine salt) and Glufosinate refers to BASTA (containing glufosinate-ammonium 200 g/l). Control 7 assesses the damage caused by the lipophilic composition with citric acid substituted for the herbicide.

| | |
|---|---|
| Control 1 | 25 g/ha glyphosate in aqueous solution with 0.1% BS 1000 |
| Control 2 | 75 g/ha glyphosate in aqueous solution with 0.1% BS 1000 |
| Control 3 | 150 g/ha glyphosate in aqueous solution with 0.1% BS 1000 |
| Control 4 | VOC RHT 70 |
| Control 5 | Esterol 123 |
| Control 6 | Glyphosate (75 g/ha), 2,4-D (150 g/ha) in aqueous solution with 0.1% BS 1000 |
| Control 7 | 20 g/L citric acid, 20 g/L 1,3-butanediol, 70 g/L dimethylcocoamine, 100 g/L Esterol 272 and VOC RHT 70 to 1 liter. |
| Control 8 | Glyphosate (75 g/ha), 2,4-D (75 g/ha) in aqueous solution with 0.1% BS 1000 |
| Control 9 | Glyphosate (150 g/ha), 2,4-D (150 g/ha) in aqueous solution with 0.1% BS 1000 |
| Control 10 | Glufosinate (50 g/ha) |
| Control 11 | Glufosinate (200 g/ha) |
| Control 12 | 2,4-D (150 g/ha) |

Method

The treatments were applied to Ryegrass and/or Spiny Emex in both standard conditions and with simulated 10 mm rain two hours after spraying. Each test had 7 replicates. The plants were assessed 14 days after spraying.

The control treatments containing herbicides were diluted in water and applied at a rate of 64 l/Ha. The test essentially non-aqueous compositions were applied directly at a rate of 10 l/Ha.

Results

A hyphen (-) means that the composition was tested in those circumstances.

| | Fresh weight (g/plant) | | | |
|---|---|---|---|---|
| Treatment | Ryegrass with no rain | Ryegrass with rain | Spiny Emex with no rain | Spiny Emex with rain |
| No treatment | 2.07 | 2.07 | 10.4 | 10.44 |
| Control 1 | 1.162 | 1.564 | - | - |
| Control 2 | 0.308 | 1.192 | 8.32 | 10.37 |
| Control 3 | 0.236 | 0.5000 | 6.04 | 9.02 |
| Control 4 | 1.142 | - | 11.6 | - |
| Control 5 | 1.443 | - | - | - |
| Control 6 | 0.417 | 1.198 | 5.53 | 9.91 |
| Control 7 | 1.50 | - | 12.3 | - |
| Control 8 | - | - | 6.93 | 10.19 |
| Control 9 | - | - | 5.71 | 8.55 |
| Control 10 | - | - | 8.59 | 11.05 |
| Control 11 | - | - | 1.26 | 10.07 |
| Control 12 | - | - | 9.27 | 7.52 |
| Composition 4. | 0.895 | - | - | - |
| Composition 5. | 0.183 | - | - | - |
| Composition 6. | 0.117 | - | - | - |
| Composition 7. | 0.339 | - | - | - |
| Composition 8. | 0.261 | - | - | - |
| Composition 9. | 0.106 | - | - | - |
| Composition 10. | 0.311 | - | - | - |
| Composition 11. | 0.292 | - | - | - |
| Composition 12. | 0.338 | 0.682 | - | - |
| Composition 13. | 0.124 | 0.254 | - | - |
| Composition 14. | 0.133 | 0.224 | - | - |
| Composition 15. | 0.390 | 0.614 | - | - |
| Composition 16. | 0.117 | 0.197 | 5.13 | 4.56 |
| Composition 17. | 0.104 | 0.321 | 2.11 | 2.95 |
| Composition 18. | - | - | 4.78 | 7.37 |
| Composition 19. | - | - | 3.71 | 4.44 |
| Composition 20. | - | - | 4.16 | 4.58 |
| Composition 21. | - | - | 3.42 | 3.26 |
| Composition 22. | 0.1543 | 0.978 | 4.08 | 6.59 |

LSD (P=0.05) 0.300

Conclusions (a) Glyphosate

At the three concentration levels of 25, 75 and 150 g/Ha, the test compositions performed better than the control treatments on Ryegrass with no rain. In rain conditions, the test compositions 12 to 17 performed significantly better than the control treatments and indeed are comparable with or outperform the control treatments 1–3 without rain.

Compositions 10 and 11 which contained water did not provide improved results over those without water.

On Spiny Emex, at the concentration levels of 75 and 150 g/Ha, test compositions 16 and 17 performed markedly better than the control treatments 2–3 in both no rain and rain conditions. The control treatments were not effective to control Spiny Emex in rain conditions, however test compositions 16 and 17 in rain conditions outperformed the control treatments without rain.

Therefore, the compositions of the invention provided rainfastness for the herbicide.

(b) Glyphosate and 2,4-D

Composition 22 on Ryegrass performed better than Control 6 both with rain and without rain.

On Spiny Emex, Compositions 20 to 22 performed better than Controls 6, 8 and 9. Again, the control treatments were not effective to control Spiny Emex in rain conditions, but the compositions of the invention in the rain were comparable or outperformed with the control treatments without rain indicating that the composition of the invention provided rainfastness for the herbicide.

(c) Glufosinate

Without rain on Spiny Emex, Composition 18 performed better than Control 10 therefore the composition of the invention provides an adjuvant effect at a concentration of 50 g/Ha of glufosinate.

In rain, Compositions 18 and 19 performed better than Controls 10 and 11 which were not effective at controlling Spiny Emex. Therefore, the compositions of the invention provided rainfastness for the herbicide.

Example 10

In this example, essentially non-aqueous compositions containing glyphosate were tested for efficacy.

The following compositions were tested.

| Composition | Glyohosate (g/L) | Dimethylcocoamine (g/L) | Polar solvent (g/L) | | Additional solvent (g/L) | | Lipophilic carrier (to 1 litre) |
|---|---|---|---|---|---|---|---|
| 23. | 21 | 79.1 | 1,3 butanediol | 24 | Breakthru OE 444 | 16 | VOC RHT 70 |
|  |  |  | Glysolv DPM | 9 | Esterol 272 | 47 |  |
|  |  |  |  |  | Span 80 | 46.5 |  |
| 24. | 5.25 | 19.8 | 1,3 butanediol | 6 | Breakthru OE 444 | 16 | VOC RHT 70 |
|  |  |  | Glysolv DPM | 2 | Esterol 272 | 21.5 |  |
|  |  |  |  |  | Span 80 | 11.5 |  |
| 25. | 2.1 | 7.91 | 1,3 butanediol | 2.4 | Breakthru OE 444 | 16 | VOC RHT 70 |
|  |  |  | Glysolv DPM | 1 | Esterol 272 | 12.5 |  |
|  |  |  |  |  | Span 80 | 5 |  |
| 26. | 21 | 90 | 1,3 butanediol | 24 | Esterol 272 | 10 | VOC RHT 70 |
|  |  |  |  |  | Teric 12A3 | 60 |  |
|  |  |  |  |  | Teric DD5 | 30 |  |
| 27. | 5.25 | 22.5 | 1,3 butanediol | 6 | Esterol 272 | 10 | VOC RHT 70 |
|  |  |  |  |  | Span 80 | 5 |  |
|  |  |  |  |  | Teric 12A3 | 15 |  |
|  |  |  |  |  | Teric DD5 | 7.5 |  |
| 28. | 2.1 | 9 | 1,3 butanediol | 2.4 | Esterol 272 | 5 | VOC RHT 70 |
|  |  |  |  |  | Span 80 | 7.5 |  |
|  |  |  |  |  | Teric 12A3 | 10 |  |
|  |  |  |  |  | Teric DD5 | 5 |  |
| 29. | 21.1 | 84.4 | 1,3 butanediol | 24.5 | Esterol 272 | 43.3 | Shell P878 |
|  |  |  | Glysolv DPM | 9.3 | Span 80 | 43.3 |  |
| 30. | 5.3 | 21.1 | 1,3 butanediol | 6.1 | Esterol 272 | 19 | Shell P878 |
|  |  |  | Glysolv DPM | 2 | Span 80 | 14 |  |
| 31. | 2.11 | 8.44 | 1,3 butanediol | 2.45 | Esterol 272 | 12.5 | Shell P878 |
|  |  |  | Glysolv DPM | 1 | Span 80 | 10 |  |
| 32. | 21.1 | 84.4 | 1,3 butanediol | 24.5 | Teric 12A3 | 45 | Shell P878 |
|  |  |  | Water (Ammonium nitrate 20) | 50 | Teric DD5 | 10 |  |
|  |  |  |  |  | Terwet 3001 | 22.5 |  |
|  |  |  |  |  | Vicamid 825 | 50 |  |
| 33. | 5.3 | 21.1 | 1,3 butanediol | 6.1 | Teric 12A3 | 45 | Shell P878 |
|  |  |  | Water (Ammonium nitrate 20) | 50 | Teric DD5 | 10 |  |
|  |  |  |  |  | Terwet 3001 | 22.5 |  |
|  |  |  |  |  | Vicamid 825 | 50 |  |
| 34. | 2.11 | 8.44 | 1,3 butanediol | 2.45 | Teric 12A3 | 45 | Shell P878 |
|  |  |  | Water (Ammonium nitrate 20) | 50 | Teric DD5 | 10 |  |
|  |  |  |  |  | Terwet 3001 | 22.5 |  |
|  |  |  |  |  | Vicamid 825 | 50 |  |

The following control treatments were used.

| | |
|---|---|
| Control 1 | 50 g/ha glyphosate in aqueous solution with 0.1% BS 1000 |
| Control 2 | 125 g/ha glyphosate in aqueous solution with 0.1% BS 1000 |
| Control 3 | 500 g/ha glyphosate in aqueous solution with 0.1% BS 1000 |

Method

The treatments were applied to ryegrass in conditions equivalent to no rain and 10 mm rain two hours after spraying. Each test had 7 replicates. The plants were assessed 14 days after spraying.

The control treatments containing herbicides were applied at a rate of 64 l/Ha according to current practice.

The test essentially non-aqueous compositions were too viscous for spraying and were diluted 1:1 with Shell P878 and sprayed at 50 l/ha.

Results

| | Fresh weight (g/plant) | |
|---|---|---|
| Treatment | Ryegrass with no rain | Ryegrass with rain |
| No treatment | 1.862 | 1.862 |
| Control 1 | 0.969 | 1.268 |
| Control 2 | 0.281 | 0.663 |
| Control 3 | 0.234 | 0.309 |
| Blank oil | 1.093 | — |
| Composition 23. | 0.217 | 0.181 |
| Composition 24. | 0.286 | 0.211 |
| Composition 25. | 0.381 | 0.389 |
| Composition 26. | 0.194 | 0.203 |
| Composition 27. | 0.284 | 0.292 |
| Composition 28. | 0.362 | 0.411 |
| Composition 29. | 0.260 | 0.218 |
| Composition 30. | 0.404 | 0.322 |
| Composition 31. | 0.323 | 0.748 |
| Composition 32. | 0.481 | 0.385 |
| Composition 33. | 0.281 | 0.208 |
| Composition 34. | 0.375 | 0.313 |

LSD (P=0.05) 0.191

Conclusions

The test results show that glyphosate is active in a non-aqueous environment with comparable or better results.

Rainfall after application is known to reduce the efficacy of certain products including glyphosate-based herbicides. This is evidenced by comparing the results for the commercial products with and without simulated rainfall as shown in the above Table where the Fresh Weight for each of the Controls 1, 2 and 3 is higher for each example where rain is applied. By contrast, the non-aqueous Compositions 23 to 30 do not show such loss of activity when simulated rainfall was applied and can be said to be rainfast.

Example 11

In this example, essentially non-aqueous compositions containing glyphosate were tested for efficacy.

The following compositions were tested. In the table the following abbreviations are used:

| | |
|---|---|
| DMC | Dimethylcocoamine (tertiary) |
| OAPA | Oleylamidopropyldimethylamine (tertiary) |
| DEA | Diethanolamine (hydrophilic) |
| MEA | Monoethanolamine (hydrophilic) |

| Composition | Glyphosate (g) | Amine (g) | | Polar solvent (g) | | Additional solvent (g) | | Lipophilic carrier (to 2 liter) |
|---|---|---|---|---|---|---|---|---|
| 35. | 10.2 | DMC | 27 | 1,3-butanediol | 10 | Esterol 272 | 60 | VOC RHT 70 |
| | | | | hexylene glycol | 12 | | | |
| 36. | 10.2 | DMC | 14 | 1,3-butanediol | 4 | Esterol 272 | 35 | VOC RHT 70 |
| | | | | 2-ethylhexanol | 4 | | | |
| | | DEA | 0.6 | Ethanol | 2 | Vicamid 825 | 35 | |
| | | | | water | 3 | | | |
| 37. | 10.2 | OAPA | 31 | 1,3-butanediol | 5 | Esterol 272 | 76 | VOC RHT 70 |
| | | | | Water | 5 | | | |
| | | | | Glysolv DPM | 7.5 | | | |
| 38. | 10.2 | OAPA | 45 | 1,3-butanediol | 5 | Vicamid 825 | 15 | VOC RHT 70 |
| | | | | water | 5 | Esterol 272 | 100 | |
| 39. | 10.2 | OAPA | 2.8 | 1,3-butanediol | 5.6 | Vicamid 825 | 30 | Prorex 36 |
| | | MEA | 4 | water | 7.5 | Esterol 272 | 32.8 | 3 and VOC RHT 70 |
| 40. | 10.2 | DMC | 2 | 1,3-butanediol | 5.6 | Vicamid 825 | 25 | Prorex 36 |
| | | MEA | 4 | water | 7.5 | Esterol 272 | 29 | 3 and VOC RHT 70 |

Composition 35 to 40 each have 0.5% w/v glyphosate. These treatments were sprayed at 50 l/ha to give 50 g/ha of glyphosate under standard conditions and with 5 mm simulated rain 2 hours after application. Control 2 was sprayed in equivalent amounts.

The above compositions are being tested against the following control treatment.

| | |
|---|---|
| Control 1 | Roundup Max (glyphosate 510 g/l as the MBA salt) diluted in water and sprayed at 64 l/ha top give 50 and 150 g/ha of glyphosate. |
| Control 2 | 50 g water, 30 g citric acid, 30 g 1,3-butanediol, 30 g hexylene glycol, 90 g Vicamid 825 , 70 g Oleylamidopropyl-dimethylamine, 210 g Esterol 272 VOC RHT 70 to 2 L. |

Results

Each test had seven replicates and the plants were assessed 14 days after spraying.

| | Fresh weight (g) | |
|---|---|---|
| Treatment | Standard conditions | 5 mm rain |
| No treatment | 3.42 | |
| Control 1 (50 g/ha) | 1.07 | 2.88 |
| Control 1 (150 g/ha) | 0.74 | 1.40 |
| Control 2 | 2.49 | 3.37 |
| Composition 35. | 1.47 | 1.85 |
| Composition 36. | 1.61 | 1.42 |
| Composition 37. | 1.16 | 1.78 |
| Composition 38. | 0.76 | 1.06 |
| Composition 39. | 0.89 | 2.60 |
| Composition 40. | 1.48 | 3.75 |

LSD (P=0.05) 0.78

Conclusion

Examples 35 to 38 all contain at least one mole equivalent of tertiary dimethylamine to each mole of glyphosate.

Examples 39 and 40 contain less than one (approx 0.16 mole equivalent for each) mole equivalent of tertiary dimethylamine to each mole of glyphosate with the remainder of the glyphosate being complexed with the hydrophilic amine monoethanolamine in accordance with the sixth aspect of the invention.

Each of the examples 35 to 40 show similar efficacy to the commercial product Round-Up Max under the Standard Conditions.

Examples 35 to 38 are less affected by simulated rainfall than examples 39 and 40 or the Control 1. The increase in fresh weight is up to 50% for examples 35 to 38 (reduction seen for 36) whilst for each of Examples 39, 40 and Control 1, the increase in fresh weight is greater than 100%. Examples 35 to 38 or compositions containing at least one mole equivalent of tertiary dimethylamine to each mole of glyphosate are more rainfast than other lipophilic compositions or the aqueous control.

Example 12

Most of the compositions shown in the previous examples have been designed to be tested at sublethal doses of the herbicide for comparative testing, or are suitable as herbicidal compositions when sprayed at rates considerably greater than 10 l/ha.

The following Compositions 41 to 46 have been prepared as examples of essentially non-aqueous herbicide compositions each containing 50 g/l of the herbicide glyphosate. These examples are considered to be suitable herbicidal compositions for spraying at 10 l/ha to provide 500 g/ha of the active.

In the table the following abbreviations are used:

| | |
|---|---|
| DMC | Dimethylcocoamine (tertiary) |
| OAPA | Oleylamidopropyldimethylamine (tertiary) |
| DEA | Diethanolamine (hydrophilic) |
| MEA | Monoethanolamine (hydrophilic) |

| Composition | Glyphosate (g) | Amine (g) | | Polar solvent (g) | | Additional solvent (g) | | Lipophilic carrier (to 100 ml) |
|---|---|---|---|---|---|---|---|---|
| 41. | 5.1 | DMC | 13.5 | 1,3-butanediol | 5 | Esterol 272 | 12.5 | VOC RHT 70 |
| | | | | hexylene glycol | 5 | | | |
| 42. | 5.1 | DMC | 13.5 | 1,3-butanediol | 5 | Esterol 272 | 12.5 | VOC RHT 70 |
| | | | | hexylene glycol | 5 | Breakthru OE444 | 0.6 | |
| 43. | 5.1 | DMC | 7 | 1,3-butanediol | 2 | Esterol 272 | 12 | VOC RHT 70 |
| | | DEA | 0.3 | 2-ethylhexanol | 2 | Vicamid 825 | 13 | |
| 44. | 5.1 | DMC | 1.0 | 1,3-butanediol | 2.8 | Vicamid 825 | 8 | VOC RHT 70 |
| | | DEA | 2.0 | water | 3.7 | Esterol 272 | 9 | |
| 45. | 5.1 | OAPA | 22.7 | 1,3-butanediol | 3.6 | Esterol 272 | 21.6 | VOC RHT 70 |
| | | | | Glysolv DPM | 5.4 | | | |
| 46. | 5.1 | OAPA | 22.7 | 1,3-butanediol | 3.6 | Esterol 272 | 21.6 | Esterol 123 |
| | | | | Glysolve DPM | 5.4 | | | |

Example 13

In this example, a composition containing glyphosate and 2,4-D was prepared.

| | |
|---|---|
| Glyphosate | 51 parts |
| 2,4-D octyl ester | 38 parts |
| Water | 2 parts |
| 1,3-butanediol | 20 parts |
| Dimethylcocamine | 121 parts |

The final composition contained 19.9% w/v glyphosate. This was a concentrated composition suitable for sale to farmers who may then further dilute the composition with additional solvents and lipophilic carriers or with a crop oil concentrate.

The word 'comprising' and forms of the word 'comprising' as used in this description does not limit the invention claimed to exclude any variants or additions.

Modifications and improvements to the invention will be readily apparent to those skilled in the art. Such modifications and improvements are intended to be within the scope of this invention.

What is claimed is:

1. An essentially non-aqueous homogeneous liquid herbicide composition comprising:
   (a) a lipophilic solvent soluble complex comprising the reaction product of:
      (i) not in excess of about 35% by weight of one or more lipophobic herbicides having an acidic moiety; and
      (ii) not in excess of about 99% by weight of one or more tertiary dimethylamines of the structure $(CH_3)_2$N—R wherein R is a substituted or unsubstituted alkyl group of at least 8 carbon atoms and wherein there is at least one mole equivalent of such amine to each mole of lipophobic herbicide;
   (b) one or more essentially non-aqueous polar solvents having low volatility;
   (c) one or more additional solvents selected from the group consisting of low to medium HLB surfactants; and
   (d) one or more lipophilic carriers.

2. A composition according to claim 1, wherein the one or more essentially non-aqueous polar solvents are present in an amount not in excess of about 60% by weight, the one or more additional solvents are present in an amount not in excess of about 90% by weight, and the one or more lipophilic carriers are present in an amount not in excess of about 99% by weight.

3. A composition according to claim 2 wherein the lipophobic herbicide is selected from the group comprising glyphosate, glufosinate, bilanafos, fosamine or mixtures thereof.

4. A composition according to claim 3 wherein the lipophobic herbicide is glyphosate.

5. A composition according to claim 3 wherein the lipophobic herbicide is glufosinate.

6. A composition according to claim 2 wherein the amount of lipophobic herbicide is not in excess of 25% by weight.

7. A composition according to claim 2 wherein the amount of lipophobic herbicide is in the range of from 0.1 to 10% by weight.

8. A composition according to claim 2 wherein the tertiary dimethylamines are selected from the group consisting of dimethylalkylamines, alkylamidoalkyldimethylamines, other substituted dimethylalkylamines and mixtures thereof.

9. A composition according to claim 2 wherein the amount of tertiary dimethylamines is in the range of from 1 to 50% by weight.

10. A composition according to claim 2 wherein the amount of tertiary dimethylamines is in the range of from 10 to 25% by weight.

11. A composition according to claim 2 wherein the essentially non-aqueous polar solvents having low volatility are selected from group consisting of butane-1,3-diol, hexylene glycol and dipropyleneglycol monomethyl ether.

12. A composition according to claim 2 wherein the amount of essentially non-aqueous polar solvent having low volatility is in the range of from 0.2 to 5% by weight.

13. A composition according to claim 2 wherein the additional solvent is selected from the group consisting of mono and di-glycerides of fat forming fatty acids, glycerol monooleate, glycerol dioleate, partial fatty acid esters of sorbitol anhydrides, sorbitan monooleate, sorbitan monolaurate, partial fatty acid esters of other polyols, pentaerythritol, polyglycerol, sugar pentitols and their anhydrides, sugar hexitols and their anhydrides, lecithin, low mole nonionic ethoxylates with alkyl or arylalkyl of 12 to 21 carbon atoms and 2 to 9 moles ethylene oxide adducted, and mixtures thereof.

14. A composition according to claim 2 wherein the amount of additional solvent is not in excess of 50% by weight.

15. A composition according to claim 14 wherein the amount of additional solvent is in the range of from 0.4 to 40% by weight.

16. A composition according to claim 2 wherein the lipophilic carrier is selected from the group consisting of petroleum fractions, vegetable oils, synthetic triglycerides, alkyl esters of fatty acids, fatty alcohols, guerbet alcohols and mixtures thereof.

17. A composition according to claim 16 wherein the lipophilic carrier is selected from the group consisting of aliphatic paraffinic light distillates or vegetable oils and their derivatives.

18. A composition according to claim 2 wherein the amount of lipophilic carrier is not in excess of 95% by weight.

19. A composition according to claim 2 further comprising one or more pesticides which are compatible with the lipophilic nature of the herbicide composition.

20. A composition according to claim 19 wherein the pesticides are selected from the group consisting of herbicides, fungicides, insecticides and mixtures thereof.

21. A composition according to claim 19 wherein the pesticide is 2,4-D.

22. A composition according to claim 2 further comprising at least one other adjuvant component.

23. A composition according to claim 22 wherein the other adjuvant components are selected from the group consisting of plant nutrients, spray drift retardants, stickers, viscosity modifiers, spreaders and mixtures thereof.

24. A concentrated essentially non-aqueous homogeneous liquid herbicide composition comprising:
   (a) a lipophilic solvent soluble complex comprising the reaction product of
      (i) not in excess of about 35% by weight of one or more lipophobic herbicides having an acidic moiety; and
      (ii) not in excess of about 99% by weight of one or more tertiary dimethylamines of the structure $(CH_3)_2$N—R wherein R is a substituted or unsubstituted alkyl group of at least 8 carbon atoms and wherein there is at least one mole equivalent of such amine to each mole of lipophobic herbicide; and (b) one or more essentially non-aqueous polar solvents having low volatility.

25. A composition according to claim 24, wherein the one or more essentially non-aqueous polar solvents are present in an amount not in excess of about 60% by weight.

26. A concentrated composition according to claim 25 further comprising not in excess of 90% by weight of one or more essentially additional solvents selected from the group consisting of low to medium HLB surfactants.

27. An essentially non-aqueous homogeneous liquid herbicide composition comprising:
(a) a lipophilic solvent soluble complex comprising the reaction product of:
  (i) not in excess of about 35% by weight of one or more lipophobic herbicides having an acidic moiety; and
  (ii) not in excess of about 99% by weight of one or more tertiary dimethylamines of the structure $(CH_3)_2$N—R wherein R is a substituted or unsubstituted alkyl group of at least 8 carbon atoms and wherein there is at least one mole equivalent of such amine to each mole of lipophobic herbicide; and
(b) one or more essentially non-aqueous polar solvents, which solvents assist the formation of the lipophilic solvent soluble complex, wherein the complex is formed in the presence of the essentially non-aqueous polar solvent but the essentially non-aqueous polar solvent may be removed after formation of the complex if desired.

28. The composition according to claim 27 wherein the one or more essentially non-aqueous polar solvents are present in an amount not in excess of about 60% by weight.

29. An essentially non-aqueous homogeneous liquid herbicide composition comprising:
(a) a lipophilic solvent soluble complex comprising the reaction product of:
  (i) not in excess of about 35% by weight of one or more lipophobic herbicides having an acidic moiety; and
  (ii) not in excess of about 99% by weight of one or more tertiary dimethylamines of the structure $(CH_3)_2$N—R wherein R is a substituted or unsubstituted alkyl group of at least 8 carbon atoms and wherein there is at least one mole equivalent of such amine to each mole of lipophobic herbicide;
(b) one or more additional solvents selected from the group consisting of low to medium HLB surfactants; and
(c) one or more lipophilic carriers.

30. A composition according to claim 29, wherein the one or more additional solvents are present in an amount not in excess of about 90% by weight, and the one or more lipophilic carriers are present in an amount not in excess of about 99% by weight.

31. An essentially non-aqueous homogeneous liquid herbicide composition comprising:
(a) a lipophilic solvent soluble complex comprising the reaction product of:
  (i) not in excess of about 35% by weight of one or more lipophobic herbicides having an acidic moiety; and
  (ii) not in excess of about 99% by weight of one or more tertiary dimethylamines of the structure $(CH_3)_2$N—R wherein R is a substituted or unsubstituted alkyl group of at least 8 carbon, wherein there is less than one mole equivalent of such amine to each mole of lipophobic herbicide;
  (iii) not in excess of about 20% by weight of one or more hydrophilic amines; wherein the total mole equivalents of the amines in (ii) and (iii) is at least equivalent to the moles of lipophobic herbicide;
(b) one or more essentially non-aqueous polar solvents;
(c) one or more additional solvents selected from the group consisting of low to medium HLB surfactants; and
(d) one or more lipophilic carriers.

32. A composition according to claim 31, wherein the one or more essentially non-aqueous polar solvents are present in an amount not in excess of about 60% by weight, the one or more additional solvents are present in an amount not in excess of about 90% by weight, and the one or more lipophilic carriers are present in an amount not in excess of about 99% by weight.

33. An essentially non-aqueous homogeneous liquid herbicide composition comprising:
(a) a lipophilic solvent soluble complex comprising the reaction product of:
  (i) not in excess of about 25% by weight of glyphosate; and
  (ii) not in excess of about 99% by weight of one or more tertiary dimethylamines of the structure $(CH_3)_2$N—R wherein R is a substituted or unsubstituted alkyl group of at least 8 carbon and wherein there is at least one mole equivalent of such amine to each mole of lipophobic herbicide;
(b) one or more essentially non-aqueous polar solvents selected from 1,3-butanediol, hexylene glycol and mixtures thereof;
(c) one or more additional solvents selected from the group consisting of low to medium HLB surfactants; and
(d) one or more lipophilic carriers selected from the group consisting of aliphatic paraffinic light distillates or vegetable oils and their derivatives.

34. A composition according to claim 33, wherein the one or more essentially non-aqueous polar solvents are present in an amount not in excess of about 60% by weight, the one or more additional solvents are present in an amount not in excess of about 90% by weight, and the one or more lipophilic carriers are present in an amount not in excess of about 99% by weight.

35. A method for improving rainfastness of a lipophobic herbicide comprising the step of formulating the lipophobic herbicide in an essentially non-aqueous composition comprising:
(a) a lipophilic solvent soluble complex comprising the reaction product of
  (i) not in excess of about 35% by weight of one or more lipophobic herbicides having an acidic moiety; and
  (ii) not in excess of about 99% by weight of one or more tertiary dimethylamines of the structure $(CH_3)_2$N—R wherein R is a substituted or unsubstituted alkyl group of at least 8 carbon atoms and wherein there is at least one mole equivalent of such amine to each mole of lipophobic herbicide;
(b) one or more essentially non-aqueous polar solvents having low volatility;
(c) one or more additional solvents selected from the group consisting of low to medium HLB surfactants; and
(d) one or more lipophilic carriers.

36. A method according to claim 35, wherein the one or more essentially non-aqueous polar solvents are present in the composition in an amount not in excess of about 60% by weight, the one or more additional solvents are present in the composition in an amount not in excess of about 90% by weight, and the one or more lipophilic carriers are present in the composition in an amount not in excess of about 99% by weight.

37. A method for treating weeds comprising the step of applying to the weeds an essentially non-aqueous sprayable herbicide composition comprising:
    (a) a lipophilic solvent soluble complex comprising the reaction product of:
        (i) not in excess of about 35% by weight of one or more lipophobic herbicides having an acidic moiety; and
        (ii) not in excess of about 99% by weight of one or more tertiary dimethylamines of the structure $(CH_3)_2$N—R wherein R is a substituted or unsubstituted alkyl group of at least 8 carbon atoms and wherein there is at least one mole equivalent of such amine to each mole of lipophobic herbicide;
    (b) one or more essentially non-aqueous polar solvents having low volatility;
    (c) one or more additional solvents selected from the group consisting of low to medium HLB surfactants; and
    (d) one or more lipophilic carriers.

38. A method according to claim 37, wherein the one or more essentially non-aqueous polar solvents are present in the composition in an amount not in excess of about 60% by weight, the one or more additional solvents are present in the composition in an amount not in excess of about 90% by weight, and the one or more lipophilic carriers are present in the composition in an amount not in excess of about 99% by weight.

39. A method for preparing an essentially non-aqueous sprayable herbicide composition comprising the steps of
    (a) combining the following reagents:
        (i) not in excess of about 35% by weight of one or more lipophobic herbicides having an acidic moiety; and
        (ii) not in excess of about 99% by weight of one or more tertiary dimethylamines of the structure $(CH_3)_2$N—R wherein R is a substituted or unsubstituted alkyl group of at least 8 carbon atoms and wherein there is at least one mole equivalent of such amine to each mole of lipophobic herbicide; and
        (iii) one or more essentially non-aqueous polar solvents having low volatility; and
    (b) combining the mixture formed in (a) with one or more additional solvents, selected from the group consisting of low to medium HLB surfactants and one or more lipophilic carriers.

40. A method according to claim 39, wherein the one or more essentially non-aqueous polar solvents are present in the composition in an amount not in excess of about 60% by weight, the one or more additional solvents are present in the composition in an amount not in excess of about 90% by weight, and the one or more lipophilic carriers are present in the composition in an amount not in excess of about 99% by weight.

41. The method according to claim 40 wherein the reagents in step (a) are combined with at least one of heating and stirring.

42. The method according to claim 40 wherein the combining in step (b) comprises stirring the mixture while warm.

\* \* \* \* \*